United States Patent [19]

Atkins

[11] Patent Number: 4,783,555

[45] Date of Patent: Nov. 8, 1988

[54] PROCESS FOR THE PRODUCTION OF A HYDRATION PRODUCT FROM AN OLEFINIC FEEDSTOCK

[75] Inventor: Martin P. Atkins, Sunbury-on-Thames, England

[73] Assignee: The British Petroleum Company p.l.c., London, England

[21] Appl. No.: 884,411

[22] Filed: Jul. 11, 1986

[30] Foreign Application Priority Data

Jul. 17, 1985 [GB] United Kingdom ............... 8518026

[51] Int. Cl.$^4$ ............................................. C07C 41/01
[52] U.S. Cl. ....................... 568/695; 568/840; 568/897; 502/64; 502/71; 502/77
[58] Field of Search .............. 568/694, 695, 897; 585/640; 428/328 T; 44/56

[56] References Cited

U.S. PATENT DOCUMENTS

| 2,805,261 | 9/1957 | Keith | 568/694 |
|---|---|---|---|
| 2,813,908 | 11/1957 | Yeung | 568/694 |
| 3,917,721 | 11/1975 | Frampton | 568/694 |
| 4,080,391 | 3/1978 | Tsumura et al. | 568/694 |
| 4,087,471 | 5/1978 | Binman | 44/56 |
| 4,413,150 | 11/1983 | Briggs | 44/56 |
| 4,507,512 | 3/1985 | Okumura | 568/897 |
| 4,528,410 | 7/1985 | Sakamoto | 568/897 |
| 4,590,294 | 5/1986 | Ballantine et al. | 568/695 |
| 4,663,662 | 8/1986 | Morton et al. | 44/56 |

FOREIGN PATENT DOCUMENTS

| 0026041 | 4/1981 | European Pat. Off. . |
|---|---|---|
| 55045 | 6/1982 | European Pat. Off. . |
| 0127486 | 12/1984 | European Pat. Off. . |
| 3337301 | 4/1984 | Fed. Rep. of Germany . |

*Primary Examiner*—Dixon, Jr. William R.
*Assistant Examiner*—James M. Hunter, Jr.
*Attorney, Agent, or Firm*—Brooks Haidt Haffner & Delahunty

[57] ABSTRACT

A hydration product is produced from an olefinic feedstock by contacting the olefinic feedstock with water under hydration conditions in the presence as catalysts of a unidimensional medium pore crystalline zeolite, for example Theta-1, ferrierite, ZSM-22, ZSM-23 or NU-10. Theta-1 is the preferred catalyst.

10 Claims, No Drawings

PROCESS FOR THE PRODUCTION OF A HYDRATION PRODUCT FROM AN OLEFINIC FEEDSTOCK

The present invention relates to a process for the production of a hydration product by the catalysed hydration of an olefinic feedstock and to the use of the product as a gasoline octane improver additive, a solvent or a chemical intermediate.

Alcohols, as produced by the hydration of olefins, are widely used as solvents and chemical intermediates.

Certain oxygenated organic compounds have been known to be potentially suitable for use as fuels for internal combustion engines for many years. Interest in such compounds as fuels declined when crude oil became relatively cheap and plentiful but has revived in recent years.

Oxygenated organic compounds may be used as fuels per se, but generally they are proposed for use in admixture with a conventional hydrocarbon fuel, thereby avoiding the need for any major modification of engines using the fuels. The oxygenated compounds may be used simply to replace part of the hydrocarbon fuel, but are more commonly proposed as octane improving additives.

For use in admixture with conventional fuels, the oxygenated organic compounds desirably should have a number of particular physical and chemical characteristics such as, total miscibility with the hydrocarbon fuel, suitable volatility and low miscibility with water. For use as an octane improving additive the oxygenated compound should also have blending octane values, both in respect of the Research Octane Number (RON) and the Motor Octane Number (MON), which enhance rather than depress the octane numbers of the neat hydrocarbon fuel.

The oxygenated organic compounds most commonly proposed for use in admixture with fuels are alcohols e.g. methanol, ethanol and butanol and ethers e.g. methyl tertiary butyl ether and tertiary amyl methyl ether. Our unpublished European application No. 86302364.4 (BP Case No. 6029), for example describes a gasoline blending composition which is either (i) a liquid reaction product containing from 70 to 99% by weight of ethers and up to 10% by weight of alcohols or (ii) a liquid reaction product containing from 40 to 70% by weight of oligomers, from 20 to 50% by weight of ehters and from 10 to 40% by weight of alcohols. In these compositions the ethers are typically dialkyl ethers and at least one of the alkyl groups is usually branched.

The production of isopropanol by the direct high pressure hydration of propylene gas with water is described in Industrial and Engineering Chemistry Vol. 30 No2, February 1938, F. M. Majewski et al "Hydration of Propylene under Pressure" pages 203 to 210. In addition to isopropanol, diisopropyl ether and polymer, e.g. propylene polymers were formed as by-products. The hydration of propylene and butylene to alcohol, ether and polymer e.g. propylene polymers, is also discussed in Journal of Chemical and Engineering Data Vol. 11 No3, July 1966, C. S. Cope "Equilibria in the Hydration of Propylene and of Butylenes" pages 379 to 383. These papers indicate that dilute acid catalysts, e.g. phosphoric acid, are suitable hydration catalysts.

In the production of the aforesaid gasoline blending additives, not only may such mineral acid catalysts be used, but also other conventional hydration catalysts, for example cation-exchangeable layered clays in which there is a metal cation, hydrogen ion-exchanged layered clays, stabilised pillared interlayered clays and cation-exchanged organic resins.

Zeolites are also known as hydration catalysts. Thus, for example, No. EP-A-0130697 describes an improved process for producing an alcohol by hydrating an olefin in the presence of a solid catalyst characterised in that the catalyst is a hydrogen-type mordenite or a hydrogen-type zeolite Y in each case having a silica to alumina molar ratio of from 20 to 500.

We have now found that certain zeolites are particularly effective catalysts for the hydration of olefins and are particularly attractive for the production of octane improving additives, because in addition to alcohols they can produce significant proportions of ethers and/or olefin oligomers.

Accordingly, the present invention provides a process for the production of a hydration product from an olefinic feedstock which process comprises contacting the olefinic feedstock with water under hydration conditions in the presence as catalyst of a unidimensional medium pore crystalline zeolite.

The hydration product comprises an alcohol and optionally also either or both of ethers and olefin oligomers. Generally, using the zeolite catalysts of the present invention the hydration product comprises alcohol, ether and olefin oligomers.

The olefinic feedstock may suitably be a single $C_2$ to $C_5$ olefin, for example ethylene, propylene, a butene or a pentene, or a mixture of at least two $C_2$ $C_5$ olefins, for example a mixture of propylene and a butene. Suitably the olefinic feedstock may comprise a refinery process stream comprising $C_2$ to $C_5$, more preferably $C_3$ and/or $C_4$ alkenes, such as, for example, a $C_3/C_4$ stream originating from the catalytic cracking of higher hydrocarbons.

The catalyst comprises a zeolite which must (i) be crystalline, (ii) be a medium pore zeolite, and (iii) have a unidimensional channel system. Crystallinity requires no further explanation, it is customarily determined by X-ray diffraction. A medium pore zeolite is one having a 10-member ring channel structure, as opposed to an 8-member (small pore) or 12-member (large pore) channel structure. A unidimentional channel system may be considered as one in which the individual channels do not communicate with other channels of similar dimensions, it may be considered as a uni-directional sieve.

The aforesaid properties (i) to (iii) may be found not only in aluminosilicate zeolites, but also in other zeolites, for example in aluminophosphates, such as SAPO-11. Suitable aluminosilicate zeolites useful as catalysts in the process of the invention include Theta-1, Ferrierite, ZSM-22, ZSM-23 and zeolite NU-10.

Theta-1, as described and claimed in our European Pat. No. 0 057 049, which is incorporated herein by reference, has the following composition in terms of the mole ratios of oxides:

$$0.9 \pm 0.2\ M_{2/n}O:Al_2O_3:xSiO_2:yH_2O \qquad (II)$$

wherein M is at least one cation having a valence n, x is at least 10, preferably at least 60, and y/x is between 0 and 25, said aluminosilicate in the calcined hydrogen-form having an X-ray diffraction pattern substantially as set forth in Table A hereinafter.

TABLE A

| 2 theta | d-spacing | Relative intensity 100 × I/I$_o$ |
|---|---|---|
| 8.15 ± 0.5 | 11.5–10.2 | 50 to 100 |
| 10.16 ± 0.5 | 8.29–9.14 | 5 to 25 |
| 12.77 ± 0.5 | 7.20–6.66 | 10 to 20 |
| 16.36 ± 0.5 | 5.58–5.25 | 5 to 15 |
| 19.42 ± 0.5 | 4.68–4.45 | 5 to 15 |
| 20.35 ± 0.5 | 4.47–4.26 | 50 to 100 |
| 24.22 ± 0.5 | 3.75–3.60 | 50 to 100 |
| 24.65 ± 0.5 | 3.68–3.54 | 30 to 90 |
| 25.75 ± 0.5 | 3.52–3.39 | 15 to 45 |
| 35.63 ± 0.5 | 2.55–2.48 | 15 to 40 | scanned up to 2 theta=36.

The crystal structure of Theta-1 is believed to be based on a C-centred orthorhombic cell of a=13.849, b=17.421 and c=5.042 Angstroms and a space group of Cmc2$_1$. The structure is believed to be similar to that of MFI-type zeolite in that they both have sets of straight 10-T ring elliptical channels. However, they differ in that the MFI-type structure has a set of sinusoidal channels (also consisting of 10-T rings) intersecting with the straight channels to create channel intersections nearly 9 Angstroms in diameter. Theta-1 has no such channel intersections and may therefore be considered as a unidirectional sieve. The channels in Theta-1 are of about 6 Angstroms diameter. The framework density of Theta-1 is 20.5 T/1000 Angstroms (T=tetrahedra).

Theta-1 may suitably be prepared by crystallisation from a mixture containing a source of silica, a source of alumina, a source of alkali metal(s), water and an organic nitrogen-containing base, such as diethanolamine, as described in the aforesaid No. EP-A-0057049. Preferably, Theta-1 is prepared by mixing a source of silica, a source of alumina, a source of alkali metal(s), water and ammonia until a homogeneous gel is formed and crystallising the gel at a temperature above 70° C. for a period of at least 2 hours, as described in our European application publication No. 0104800, the content of which is incorporated herein by reference.

Natural or synthetic ferrierite may be used. Synthetic ferrierite may suitably be obtained by the process described in our British Pat. No. 1,436,524 which involves hydrothermal crystallisation from an aqueous gel containing an alkali or alkaline earth metal hydroxide, alumina or alkali metal aluminate, a colloidal silica sol and N-methyl pyridinium hydroxide in defined proportions. The description of the aforesaid No. GB-A-1,436,524 is incorporated herein by reference.

The zeolite, ZSM-22 is described in No. EP-A-0102716, which is incorporated herein by reference.

The zeolite ZSM-23 and its preparation is described in U.S. Pat. No. 4,076,842, the content of which is incorporated by reference herein.

The zeolite NU-10 and its preparation is described in European patent application publication No. 0065400, the content of which is incorporated by reference herein.

Of the aforesaid zeolites, Theta-1 and ferrierite are preferred, and Theta-1 is even more preferred for use as the catalyst in the process of the invention.

As prepared, aluminosilicate zeolites may contain cations other than those described in connection with their use as adsorbents, which cations may arise for example from the mineralising agent and/or inorganic base and/or the nitrogen-containing base used in the preparation of the material. The tectometallosilicate may also contain residual nitrogen-containing base lodged in the pores and/or deposited on the surface thereof and also molecules of the liquid medium employed in its preparation. Before use as a catalyst, it is desirable that residual organic base and liquid medium be removed by calcining the aluminosilicate, suitably at a temperature in the range from 300° to 700° C. Furthermore, it is generally preferred that the original cations be cation-exchanged with more desirable cations, for example hydrogen ions. Techniques for cation-exchanging zeolites and separating the cation-exchanged zeolite from the exchange media are now well established in the art and require no further elaboration.

As regards hydration conditions, the temperature may suitably be in the range from 100 to 350, preferably from 150° to 250° C., the pressure may suitably be in the range from 5 to 200 bar, preferably from 50 to 100 bar. The molar ratio of water to olefin may suitably be in the range from 1:1 to 10:1, more preferably from 2:1 to 6:1. In the event that the hydration product is to be used as an octane improver additive, it is preferred to reduce the amount of water employed to the minimum consistent with the formation of a hydration product because excess water is undesirable.

The process may be operated in the liquid or the vapour phase using a fixed bed or moving bed catalyst and either as a batch process or a continuous process. The proportions of alcohol, ether and olefin oligomer in the product will depend on many factors, including the mode of operation, the temperature, pressure and residence time employed, the catalyst and the olefinic feedstock.

The hydration process of the present invention may form the second step in a two-step process wherein the first step comprises contacting a hydrocarbon mixture comprising C$_3$ and C$_4$ olefins including isobutene with methanol and an acidic catalyst under conditions whereby isobutene is selectively converted to methyl-tertiarybutyl ether and the remaining C$_3$ and C$_4$ olefins are substantially unchanged, the unchanged olefins being passed to the second step.

In another aspect the present invention also provides an octane improver additive comprising the hydration product obtained by the process as hereinbefore described.

The octane improver additive preferably comprises dialkyl ethers, alkanols and olefin oligomers derived from C$_3$ and/or C$_4$ alkenes. The relative proportions of the components are preferably as follows:

| Component | Parts By Weight |
|---|---|
| Alkanol | 5–50 |
| Dialkyl ether | 5–50 |
| Oligomers | 10–50 | the weight ratio of oxygenates to oligomers being from 1:1 to 2:1.

It is preferred to dry the hydration product before use as an octane improver additive. This may be achieved by conventional methods. Alternatively, drying may be accomplished by contacting the hydration product with a material capable of removing water by chemical reaction converting the material to a product which itself functions as an octane improver additive, for example dimethoxy propane which is converted by reaction with water into methanol and acetone.

In yet another aspect the present invention provides a fuel composition comprising (A) a major proportion of a gasoline and (B) a minor proportion of an octane improver additive as hereinbefore described.

The fuel composition preferably comprises from 1 to 30, more preferably 10 to 20, parts by volume of the octane improving additive per 100 parts by volume of gasoline. The additive may be added to and blended with the gasoline using known techniques.

The fuel composition may comprise any gasoline. It may for example be a straight run gasoline or a cat cracked spirit or a mixture thereof. Suitably the gasoline has, before the addition of the octane improver, a Research Octane Number (RON) of from 80 to 105, preferably from 90 to 98, and a Motor Octane Number (MON) of from 75 to 95, preferably from 80 to 88. The gasoline may suitably contain the following proportions of olefins, aromatics and saturates:
Aromatics—20 to 60% by volume
Saturates—20 to 70% by volume
Olefins—0 to 30% by volume Conventional additives, for example anti-knock agents, such as tetra-ethyl lead, scavengers and antioxidants may be included in the compositions. Other oxygenated compounds, for example methanol, may also be included in the compositions. Suitably methanol may be incorporated in an amount from 3 to 5 parts by volume per 100 parts by volume of gasoline.

The invention will now be further illustrated by reference to the following Examples.

EXAMPLE 1

A suspension of the hydrogen form of Theta-1 (2 g), prepared as described in No. EP-A-0104800 and having a silicon to aluminium ratio of 35 to 1, in water (50 cm$^3$) and propene (40 cm$^3$) was stirred under 40 bar pressure of nitrogen at 200° C. for 2 hours in an autoclave. The total liquid product (56 g) was collected and analysed by gas chromatography. It contained 11.0 wt % propan-2-ol in the aqueous product. An oily layer containing propan-2-ol, diisopropyl ether and propene oligomers was also obtained.

EXAMPLE 2

A suspension of the hydrogen form of ferrierite (2 g), prepared as described in British Pat. No. 1,436,524 and having a silicon to aluminium ratio of 14 to 1, in water (50 cm$^3$) and propene (40 cm$^3$) was stirred under 40 bar pressure of nitrogen at 200° C. for 2 hours in an autoclave. The total liquid product (53 g) was collected and analysed by gas chromatography. It contained 10.1 wt % propan-2-ol in the aqueous product. An oily layer containing propan-2-ol, diisopropyl ether and propene oligomers was also obtained.

COMPARISON TEST 1

A suspension of the hydrogen form of mordenite (2 g) as supplied by the Norton Chemical Company in water (50 cm$^3$) and propene (40 cm$^3$) was stirred under 40 bar pressure of nitrogen at 200° C. for 2 hours in an autoclave. The total liquid product (56 g) was collected and analysed by gas chromatography. It contained 3.8 wt % propan-2-ol in the aqueous product. No oily layer was obtained.

COMPARISON TEST 2

A suspension of the hydrogen from of ZSM-5 (2 g), prepared as described in No. EP-A-0030811 and having a silicon to aluminium ratio of 16 to 1 in water (50 cm$^3$) and propene (40 cm$^3$) was stirred under 40 bar pressure of nitrogen at 200° C. for 2 hours in an autoclave. The total liquid product (54 g) was collected and analysed by gas chromatography. It contained 4.9 wt % propan-2-ol in the aqueous product. No oily layer was obtained.

I claim:

1. A process for the production of a hydration product from an olefinic feedstock which process comprises contacting the olefinic feedstock with water under hydration conditions in the presence as catalyst of a unidimensional medium pore crystalline zeolite, said zeolite being Theta-1, ZSM-22, or NU-10.

2. A process according to claim 1 wherein the zeolite is Theta-1.

3. A process according to claim 1 wherein the olefinic feedstock is selected from the group consisting of ethylene, propylene, a butene a pentene, and a mixture of at least two thereof.

4. A process according to claim 3 wherein the olefinic feedstock is refinery process stream selected from the group consisting of C$_3$ and C$_4$ alkenes and mixtures thereof.

5. A process according to claim 1 wherein the zeolite is in the hydrogen-form.

6. A process according to claim 1 wherein the hydration conditions are a temperature in the range from 100 to 350° C. and a pressure inthe range from 5 to 200 bar.

7. A process according to claim 6 wherein the temperature is in the range from 150° to 250° C. and the pressure is in the range from 50 to 100 bar.

8. A process according to claim 1 wherein the molar ratio of water to olefin is in the range from 1:1 to 10:1.

9. A process according to claim 1 which process forms the second step of a two-step process in which the first step comprises contacting a hydrocarbon mixture comprising C$_3$ and C$_4$ olefins including iosbutene with methanol and an acidic catalyst under conditions whereby isobutene is selectively converted to methyl-tertiarybutyl ether and the remaining C$_3$ and C$_4$ olefins are substantially unchanged, the unchanged olefins being passed to the second step.

10. A process for the production of a hydration product from an olefinic feedstock which comprises contacting the olefinic feedstock with water under hydration conditions in the presence of a catalyst consisting essentially of a unidimensional medium pore ZSM-23 crystalline zeolite.

* * * * *

UNITED STATES PATENT AND TRADEMARK OFFICE
CERTIFICATE OF CORRECTION

PATENT NO. : 4,783,555
DATED      : November 8, 1988
INVENTOR(S) : Martin P. Atkins It is certified that error appears in the above-identified patent and that said Letters Patent is hereby corrected as shown below:

Col. 1, l. 49, correct the spelling of the word "ethers"

Col. 2, l. 33, should read "..C2 to C5.."

Claim 1, l. 4, should read "..in the presence of a catalyst.."

Claim 1, l. 6, there should not be a comma after "ZSM-22"

Claim 6, l. 3, there should be a space between the words "in the"

Signed and Sealed this

Thirteenth Day of June, 1989

Attest:

DONALD J. QUIGG

Attesting Officer

Commissioner of Patents and Trademarks